(12) United States Patent
Kelley

(10) Patent No.: US 7,062,077 B1
(45) Date of Patent: Jun. 13, 2006

(54) SCANNER DENSITOMETER AND DATA EVALUATION METHOD

(75) Inventor: Charles David Kelley, Lumberton, TX (US)

(73) Assignee: Helena Laboratories Corporation, Beaumont, TX (US)

( * ) Notice: Subject to any disclaimer, the term of this patent is extended or adjusted under 35 U.S.C. 154(b) by 435 days.

(21) Appl. No.: 09/695,416

(22) Filed: Oct. 25, 2000

Related U.S. Application Data

(60) Provisional application No. 60/162,121, filed on Oct. 29, 1999.

(51) Int. Cl.
*G06K 9/00* (2006.01)

(52) U.S. Cl. ...................... 382/128; 382/169

(58) Field of Classification Search ............... 382/128, 382/133, 129, 134, 131, 132, 169; 128/922; 250/455.11, 461.2, 491.1, 252.1, 226, 363.02; 356/34, 40, 39; 372/10, 13; 600/309, 320; 73/1.02; 358/505, 474, 489, 493, 494; 378/12, 378/146, 4; 377/10

See application file for complete search history.

(56) References Cited

U.S. PATENT DOCUMENTS

| | | | | |
|---|---|---|---|---|
| 4,599,565 A | * | 7/1986 | Hoenninger et al. | 324/309 |
| 5,149,960 A | * | 9/1992 | Dunne et al. | 250/226 |
| 5,563,985 A | * | 10/1996 | Klassen et al. | 358/1.9 |
| 5,717,778 A | * | 2/1998 | Chu et al. | 382/133 |
| 5,771,105 A | * | 6/1998 | Rust et al. | 358/2.99 |
| 5,827,942 A | * | 10/1998 | Madsen et al. | 73/1.82 |
| 5,898,505 A | * | 4/1999 | Lin et al. | 358/3.1 |
| 5,949,899 A | * | 9/1999 | Ng | 382/129 |
| 5,960,081 A | * | 9/1999 | Vynne et al. | 713/176 |
| 5,974,181 A | * | 10/1999 | Prieto | 382/232 |
| 6,072,510 A | * | 6/2000 | Ogletree et al. | 347/131 |
| 6,081,209 A | * | 6/2000 | Schuyler et al. | 341/51 |
| 6,122,442 A | * | 9/2000 | Purcell et al. | 345/620 |
| 6,317,508 B1 | * | 11/2001 | Kramer et al. | 382/124 |
| 6,507,664 B1 | * | 1/2003 | Anderson et al. | 382/129 |
| 6,580,816 B1 | * | 6/2003 | Kramer et al. | 382/124 |
| 6,586,750 B1 | * | 7/2003 | Montagu et al. | 250/458.1 |

(Continued)

FOREIGN PATENT DOCUMENTS

WO   WO 94/18800   8/1994

(Continued)

OTHER PUBLICATIONS

Gonzalez et al., Digital Image Processing, §4.1.1 Spatial Domain Methods, 1992, pp. 162-164 (Addison-Wesley Publishing Co., Reading Massachusetts).

*Primary Examiner*—Barry Choobin
(74) *Attorney, Agent, or Firm*—Akerman Senterfitt

(57) ABSTRACT

Optically scanned data forms an image stored in a computer memory represented as an array having at least two dimensions. The stored image is subjected to virtual scanning. Thus a subset of the array is defined as a portion of the image having first and second dimensions. The value of the subset is derived, the subset is then incremented, and the value of the incremented subset is determined. The steps of incrementing and deriving the value of the incremented subset are repeated. The derived values of the data are compared to a calibrated standard, to create adjusted values of data. The adjusted data values, in the case of electrophoresis, represent the scanned sample which has been subjected to electrophoresis. Thereafter, the adjusted data values can be integrated or otherwise processed.

21 Claims, 4 Drawing Sheets

| 8 | 11 | 15 | 17 | 17 | 12 | 9 |
|---|----|----|----|----|----|---|
| 10 | 15 | 17 | 20 | 18 | 10 | 5 |
| 11 | 29 | 29 | 31 | 27 | 13 | 10 |
| 10 | 16 | 22 | 28 | 25 | 14 | 8 |
| 8 | 14 | 18 | 25 | 24 | 15 | 10 |
| 7 | 12 | 19 | 21 | 22 | 15 | 9 |
| 9 | 10 | 16 | 20 | 19 | 13 | 7 |

Average = $\frac{10 + 15 + 11 + 29 + 10 + 16 + 8 + 14 + 7 + 12}{10}$ = 13.2

| 8 | 11 | 15 | 17 | 17 | 12 | 9 |
|---|----|----|----|----|----|---|
| 10 | 15 | 17 | 20 | 18 | 10 | 5 |
| 11 | 29 | 29 | 31 | 27 | 13 | 10 |
| 10 | 16 | 22 | 28 | 25 | 14 | 8 |
| 8 | 14 | 18 | 25 | 24 | 15 | 10 |
| 7 | 12 | 19 | 21 | 22 | 15 | 9 |
| 9 | 10 | 16 | 20 | 19 | 13 | 7 |

Average = $\frac{15 + 17 + 29 + 29 + 16 + 22 + 14 + 18 + 12 + 19}{10}$ = 19.1

U.S. PATENT DOCUMENTS

| | | | | |
|---|---|---|---|---|
| 6,690,458 B1* | 2/2004 | Schorr | ...................... | 356/141.5 |
| 6,724,417 B1* | 4/2004 | Hillis et al. | ............... | 348/14.16 |
| 6,876,383 B1* | 4/2005 | Beitscher | ................. | 348/218.1 |
| 2001/0043728 A1* | 11/2001 | Kramer et al. | ............... | 382/124 |
| 2002/0074512 A1* | 6/2002 | Montagu et al. | ......... | 250/458.1 |
| 2002/0154799 A1* | 10/2002 | Anderson et al. | ........... | 382/128 |
| 2003/0141443 A1* | 7/2003 | Spears et al. | ............... | 250/234 |

FOREIGN PATENT DOCUMENTS

| | | |
|---|---|---|
| WO | WO 98/32004 | 7/1998 |

* cited by examiner

FIGURE 1

| INDEX | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| REFERENCE VALUE | 0 | 2 | 4 | 6 | 8 | 10 | 12 | 14 | 15 | 16 | 17 | 19 | 22 | 24 | 25 | 26 | 29 | 31 | 33 | 35 | 37 | 39 | 41 | 43 |

FIGURE 2

| 8 | 11 | 15 | 17 | 17 | 12 | 9 |
|---|----|----|----|----|----|---|
| 10 | 15 | 17 | 20 | 18 | 10 | 5 |
| 11 | 29 | 29 | 31 | 27 | 13 | 10 |
| 10 | 16 | 22 | 28 | 25 | 14 | 8 |
| 8 | 14 | 18 | 25 | 24 | 15 | 10 |
| 7 | 12 | 19 | 21 | 22 | 15 | 9 |
| 9 | 10 | 16 | 20 | 19 | 13 | 7 |

$$\text{Average} = \frac{10 + 15 + 11 + 29 + 10 + 16 + 8 + 14 + 7 + 12}{10} = 13.2$$

FIGURE 3

| 8  | 11 | 15 | 17 | 17 | 12 | 9  |
|----|----|----|----|----|----|----|
| 10 | 15 | 17 | 20 | 18 | 10 | 5  |
| 11 | 29 | 29 | 31 | 27 | 13 | 10 |
| 10 | 16 | 22 | 28 | 25 | 14 | 8  |
| 8  | 14 | 18 | 25 | 24 | 15 | 10 |
| 7  | 12 | 19 | 21 | 22 | 15 | 9  |
| 9  | 10 | 16 | 20 | 19 | 13 | 7  |

$$\text{Average} = \frac{15 + 17 + 29 + 29 + 16 + 22 + 14 + 18 + 12 + 19}{10} = 19.1$$

FIGURE 4

| 8 | 11 | 15 | 17 | 17 | 12 | 9 |
|---|----|----|----|----|----|---|
| 10 | 15 | 17 | 20 | 18 | 10 | 5 |
| 11 | 29 | 29 | 31 | 27 | 13 | 10 |
| 10 | 16 | 22 | 28 | 25 | 14 | 8 |
| 8 | 14 | 18 | 25 | 24 | 15 | 10 |
| 7 | 12 | 19 | 21 | 22 | 15 | 9 |
| 9 | 10 | 16 | 20 | 19 | 13 | 7 |

$$\text{Average} = \frac{17 + 20 + 29 + 31 + 22 + 28 + 18 + 25 + 19 + 21}{10} = 23$$

SCANNER DENSITOMETER AND DATA EVALUATION METHOD

CROSS-REFERENCE TO RELATED APPLICATION

This application claims the priority of U.S. Provisional Application No. 60/162,121 filed Oct. 29, 1999.

BACKGROUND

This invention relates to a scanner densitometer and to an improvement in scanning densitometry. This invention further relates to a method of evaluation of data.

In various fields including but not limited to clinical laboratory diagnosis, a sample or specimen is subjected to densitometry as part of the processing and, more particularly, as part of the evaluation of the sample or specimen. By way of example and not by way of limitation, blood samples may be subjected to electrophoresis and, thereafter, quantitatively evaluated by optical densitometry. The foregoing, however, is not intended as a limitation on the type of sample (blood) nor the processing of the sample (electrophoresis) nor the precise use of the densitometer (quantitative evaluation).

The present invention, which is, in its broadest form, a method of data evaluation, is described in the context of a sample which has been subjected to electrophoresis, again with the express understanding that such explanation is not intended as a limitation but is merely to explain the principles of the invention.

A sample is placed on a gel plate which is understood to refer to an electrophoresis gel and any applicable support or backing. The sample or samples on the gel plate is (are) subjected to electrophoresis. A stain may be applied as is conventional, By way of example and not by limitation, a variety of stains such as Ponceau S, Acid Blue Amido, Fat Red, Oil Red O, Commassie, Acid Violet and stains for LSTLC plates have been used in electrophoresis. In broader terms, the data to be evaluated is placed on a carrier. Then the gel plate (carrier) is placed on a scanner such as that manufactured by Epson. Preferably the gel plate is stationary in the scanner rather than feeding the gel plate past a stationary platen. The scanner takes an image of the gel plate which image is digitized and stored in a computer memory such as a RAM as a multi-dimensional array. Each "element" of the array is of a first size. One example would be a size of 0.0127 cm by 0.0127 cm for each element of the array. Each element of the array is frequently referred to as a pixel. Thus the data to be evaluated is stored as an array of pixels.

In conventional densitometry, such as using the Cliniscan® manufactured by Helena Laboratories Corporation of Beaumont, Tex., there is a physical scanning of the sample, after the electrophoresis and any staining steps, as part of the densitometry process, and the optical density of each part of the image is determined. In the present invention, scanning occurs in the computer memory, i.e., there is virtual scanning of the image. By way of example and not by way of limitation, a virtual "slit" of a given size may be used, e.g., 4.0 mm high×0.4 mm wide. This "slit" is equivalent to 31 image elements in height and 3 image elements in width. Thus at any one time the slit sees a subset of the array which is 93 elements or pixels. The optical data for all 93 elements are averaged to provide a resulting "value". In some preferred embodiments the virtual slit has a first dimension at least five times greater than the second dimension.

Before continuing with the explanation of the virtual scanning, the use of this "value" will be described. The scanner is calibrated so that the results of the virtual scanning correspond to the well-known and historically relied upon results of conventional densitometry (or any other process for which the data is to be evaluated) through the creation and use of a look-up table. To accomplish the calibration so that the look-up table can be created, a continuously variable, neutral density slide, having an optical density which ranges from 0.04 (which is 92% transmissivity) to 2.00 (which is 1.0% transmissivity) is used as a calibration device. The slide is first scanned in a conventional manner, e.g., a densitometer using traditional optics such as an incandescent lamp, lens, physical slit, filter and photocell, to establish a reference curve for the slide. The reference curve or data is stored in a RAM or other memory device. The same calibration slide is then processed by digitizing an image in the scanner and a second curve is generated based on virtual scanning. The scanner uses a 12 bit, analog to digital converter, and each data point or pixel has a value between 0 and 4095 which represents the gray level of the pixel, with 0 corresponding to white and 4095 corresponding to black. Thus there are 4096 potential values which is $2^{12}$. For each data point generated by virtual scanning of the calibration slide (i.e., the second curve), the computer compares the data based on the virtual scanned value with the reference curve value (created by traditional scanning of the calibration slide) and makes the appropriate entry in the look-up table also in the RAM or memory device.

As an example, at the $100^{th}$ data point or pixel, if the virtual scanned value of the calibration slide is 127 but the reference curve value (the traditional scanning of the calibration slide) for that same $100^{th}$ data point was 210, then in the look-up table, the value (number) 210 is stored as corresponding to scanner value 127. Thereafter, when scanning an actual sample, a virtual scanner value of 127 is interpreted as the value 210. In this fashion, the scanner of the present invention is calibrated so that the results correspond to the results of conventional scanning densitometry.

Referring back to the explanation of the virtual scanning, a value is derived for all the elements within the virtual slit, and this derived value is used to enter the look-up table. Preferably, the value is the mathematical average for all the elements (pixels) within the virtual slit which is used to enter the look-up table. The corresponding number calibrated or reference value in the look-up table is used as the value for that specific data point. Then, the virtual slit is moved (indexed) one element or pixel, and the process repeated. The virtual scanning can be done preferably in one direction, e.g., the x-direction which is along the length of the sample, or in multiple directions. In either event, the process is repeated until a value is determined for each data point. Thereafter, the data is processed e.g., integrated, as in a traditional densitometer. The disclosures of various United States Patents relating to scanning densitometers, such as Nos. 4,720,788; 4,810,348; 4,986,891; and 4,954,237 are hereby incorporated by reference.

BRIEF DESCRIPTION OF THE FIGURES

FIG. 1 is an illustration of a partial look-up table created as the result of the calibration generally described above; and FIGS. 2, 3 and 4 each illustrate, on a reduced scale, virtual scanning of a series of data points.

DETAILED DESCRIPTION

Referring to FIG. 1, a partial look-up table includes upper and lower entries, identified for clarity as index and reference value. The "reference value" entries are based upon the result of calibration as described above. Thus the "reference value" is the look-up table which is created for the specific scanner. It is feasible to store the "reference values" from conventional scanning in a ROM. Then, on a daily (or more frequently if desired) basis, the neutral density calibration slide referred to above may be process through the scanner to create the look-up table. In this fashion, any aging or deterioration of the optics of the scanner will be taken into account. Thus, with reference to FIG. 1, the "index" numbers will be the result of scanning and analog to digital conversion of the neutral calibration slide on the densitometer. The "index" numbers therefore represent the "entry" points into the look-up table.

Then, after the look-up table has been created, the sample to be evaluated is scanned, and the image digitized and stored in the computer memory. Then, using the principles of this present invention, the data is evaluated. The following are three examples.

Referring next to FIG. 2, after the image of the sample has been digitized and stored in the computer memory, as previously mentioned, the virtual slit is used to scan the image in memory. In FIG. 2, an array of 49 pixels (7×7) is illustrated although, in practice, an array of 1040×1040 pixels is preferred. The virtual slit is illustrated as a rectangular box 5 pixels high by 2 pixels wide. Again, the virtual slit preferably has a first dimension at least five times greater than the second dimension, and a preferred virtual slit is 31×3.

In the example of FIG. 2, the derived value, which in this example is the mathematical average of the 10 pixels is 13.2 and this is rounded to the nearest whole number, 13. Then, the 13 is the "index" number for entry into the look-up table; at the index number 13, the "reference value" in the look-up table is 22 (FIG. 1) and thus the first data point has a value of 22. For clarification, this is an indication that by using traditional scanning, the value of the first data point would be 22.

FIG. 3 illustrates the incremental movement of the virtual slit in the x direction for evaluation of the second data point. In FIG. 3, the average of the 10 pixels within the virtual slit is 19.1 (rounded to 19) and, using 19 as the index, (FIG. 1) the "reference value" of this second data point in the look-up table is 35.

FIG. 4 illustrates the incremental movement of the virtual slit in the x direction for evaluation of the third data point. In FIG. 4, the average of the 10 pixels within the virtual slit is 23 and, using 23 as the index, (FIG. 1) the "reference value" of this third data point in the look-up table is 43.

According to the foregoing explanation, each "data point" on the scanned curve or image, is digitized and converted to a "reference value" from the look-up table. In the example where a 31×3 pixel virtual slit is used, one end point of the curve (e.g., the starting point) may be evaluated with the first virtual slit, and as the virtual slit approaches the second end point of the curve, the last two virtual slits may be 31×2 pixels and 31×1 pixels, respectively.

After the entire image has been scanned and all data points determined, the data in the computer memory, which is now based on the values obtained from the look-up table, is processed. In densitometry in the clinical laboratory, for example, the values determined by scanning are used as data points on a curve and the data is integrated, i.e., the area under the curve determined. Areas under portions of the curve may, of course, be of significance depending on the location of peaks and valleys along the curve and the type of test being conducted.

The principles of the present invention can be applied to the various types of commercially available scanners but are not intended to be limited in that fashion. The three types of scanners are first, those known as flatbed scanners, where the sample is stationary; second, those where the sample moves along a generally straight path; and third, those where the sample follows a curved path. Similarly, the principles of the present invention are not restricted to densitometry, but are a method of data evaluation which has broad applicability, especially where there is a "standard" to which the evaluated data may be compared.

What is claimed is:

1. A method of evaluating data which has been scanned to create an image which is stored in a memory represented as an array having at least two dimensions, comprising:
    (a) defining a subset of the array as a portion of the image having at least first and second dimensions;
    (b) deriving a value for the defined subset of the array;
    (c) moving a position of the subset in at least one direction without increasing the overall dimensions of the subset;
    (d) deriving a value for the moved subset of the array; and
    (e) repeating steps (c) and (d) to obtain derived values for additional subsets of the image;
    wherein the first dimension is greater than the second dimension.

2. The method according to claim 1, wherein the step of moving is along a single direction.

3. the method according to claim 1, wherein the derived values for each subset of the scanned image are stored in a computer memory.

4. The method according to claim 1, including the steps of creating a look-up table for calibrating the scanned image to a standard, and substituting the value in the look-up table for the derived values.

5. The method according to claim 1, wherein each portion of the array represents the gray level of the corresponding portion of the image.

6. The method according to claim 1, wherein the step of deriving includes taking the mathematical average of the gray level for each portion of the array in the subset.

7. The method according to claim 1, wherein the data has been scanned using a scanner selected from the group consisting of (a) flatbed scanners, (b) scanners where the data moves along a generally straight path, and (c) scanners where the data moves along a curved path.

8. The method according to claim 1, wherein the data represents a sample which has been subjected to electrophoresis.

9. The method according to claim 1, wherein the first dimension is at least ten times greater than the second dimension.

10. The method according to claim 1, including the steps of creating a look-up table for calibrating the scanned image to a standard, and substituting the value in the look-up table for the derived values, wherein the standard is a neutral density optical calibrator.

11. The invention according to claim 1, wherein the scanned image is converted into a plurality of data points defining a curve.

12. The invention according to claim 11, wherein the area under the curve is determined by integration.

13. A method of virtual scanning of an image stored as data in a memory, the data represented as an array having at least two dimensions, wherein each element of the array is defined as a pixel, comprising:

(a) defining a subset of the array as a number of pixels oriented in at least first and second dimensions;

(b) deriving a value for the optical density of the pixels in the defined subset of the array;

(c) moving a position of the subset in at least one direction without increasing the number of pixels in the subset;

(d) deriving a value for the optical density of the pixels in the moved subset of the array; and (e) repeating steps (c) and (d) to obtain derived values for the optical density for additional subsets of the image;

wherein the first dimension is greater than the second dimension.

14. The method as defined in claim 13, including the steps of creating a look-up table for calibrating the scanned image to a standard, and substituting the value in the look-up table for the derived values, wherein the standard is a neutral density optical calibrator.

15. The method as defined in claim 13, wherein the step of deriving includes taking the mathematical average of the gray level of the optical density of each pixel in the subset.

16. The invention according to claim 13, wherein the derived values correspond to a plurality of data points defining a curve.

17. The invention according to claim 16, wherein the area under the curve is determined by integration.

18. The method according to claim 13, wherein the data has been scanned using a scanner selected from the group consisting of (a) flatbed scanners, (b) scanners where the data moves along a generally straight path, and (c) scanners where the data moves along a curved path.

19. The method of claim 13, wherein the subset of the array has a first dimension at least ten times greater than the second dimension.

20. The method of claim 1, wherein the first dimension is at least five times greater than the second dimension.

21. The method of claim 13, wherein the first dimension is at least five times greater than the second dimension.

* * * * *